United States Patent [19]
Arenson et al.

[11] Patent Number: 5,228,069
[45] Date of Patent: Jul. 13, 1993

[54] DUAL SLICE SCANNER

[75] Inventors: Jerome S. Arenson; Reuven Levinson; David Freundlich, all of Haifa, Israel

[73] Assignee: Elscint Ltd., Haifa, Israel

[21] Appl. No.: 531,053

[22] Filed: May 31, 1990

[30] Foreign Application Priority Data

Jun. 4, 1989 [IL] Israel .................................. 090521

[51] Int. Cl.$^5$ .............................................. G21K 1/12
[52] U.S. Cl. ........................................ 378/19; 378/4; 378/11
[58] Field of Search ................ 378/4, 11, 14, 17, 19, 378/24, 27, 22, 25, 23

[56] References Cited

U.S. PATENT DOCUMENTS

| | | | |
|---|---|---|---|
| 4,160,167 | 7/1979 | Weiss et al. | 378/19 |
| 4,352,986 | 10/1982 | Pfeiler | 378/24 |
| 4,442,489 | 4/1984 | Wagner | 378/19 |
| 4,485,481 | 11/1984 | Takano | 378/19 |
| 4,542,519 | 9/1985 | Sugimoto | 378/19 |
| 4,754,468 | 6/1988 | Mori | 378/19 |
| 4,965,726 | 10/1990 | Heuscher et al. | 364/413.13 |
| 5,022,060 | 6/1991 | Trotel | 378/19 |

FOREIGN PATENT DOCUMENTS

| | | | |
|---|---|---|---|
| 2717349 | 10/1978 | Fed. Rep. of Germany | 378/19 |
| 0206996 | 12/1983 | Japan | 378/19 |
| 1528574 | 10/1978 | United Kingdom | 378/19 |

Primary Examiner—David P. Porta
Assistant Examiner—Don Wong
Attorney, Agent, or Firm—Sandler Greenblum & Bernstein

[57] ABSTRACT

A CT scanner using a rotate-rotate mode wherein the detector is designed to simultaneously detect X-rays that have traversed multiple-planar sections in a patient being scanned.

8 Claims, 3 Drawing Sheets

DUAL SLICE SCANNER

FIELD OF THE INVENTION

This invention is concerned with computerized tomographic scanners and more particularly with tomographic scanning systems equipped to simultaneously acquire multiple slice data in a single scan.

BACKGROUND OF THE INVENTION

Early CT scanners that were used for scanning the brain had only a single detector and a single pencil beam X-ray source. The source and detector were repeatedly translated across the head rectilinearly a short distance and then rotated to acquire the plurality of views required to obtain an image. The early scanners required about 300 seconds to complete a 180 degree scan. Historically the next advance in scanners, known as "second generation" scanners also used a two motion system, but improved the data acquisition speed to below 20 seconds through the use of an array of detectors and a fan beam X-ray source. Twenty seconds is a normal breath holding period; and thus, the second generation tomographic scanners managed to reduce motion blurring and artifacts due to respiration.

Third generation CT scanners also known as rotate-rotate scanners used fan beam X-ray sources and an array of detectors that rotated simultaneously about the subject. The scan time of the third generation scanners in general is under 5 seconds. The fourth generation CT scanners also use a fan beam X-ray source that rotate within a circle of stationary detectors occupying a full 360 degree circle around the subject. Hence, the successive generations of CT scanners increased the scan speed to decrease the scanning time. Each generation used more detectors in the detector arrays and thereby substantially increased the costs of the system. The increased number of detectors, of course, increased the spatial resolution. Thus in successive gnerations the speed of operation and the cost of the scanners were increased while the spatial resolution was improved.

One method used to increase the speed of the earlier scanners; i.e., first generation scan CT scanners was the use of tandem detectors to obtain dual slices in a single scan. This practice was discontinued when detector arrays were used. Thus, after the scan speed improvement of the second generation it was generally assumed by those skilled in the art that there was no longer a need to acquire data for two slices simultaneously.

An important factor mitigating against the simultaneous acquisition of dual slice data in a single scan is that to accomplish such dual slice imaging it is necessary to increase the number of detectors. Each detector, of course, normally requires a separate channel with all of the front end electronics and hardware to support the detector. Hence, each added detector substantially increases the cost of the tomographic equipment. Thus, while dual slice equipment saves time it does substantially increase the cost and in the past has increased artifacts caused by the scanning operation. Accordingly, those skilled in the art have not used simultaneous dual slice features since about the time of the introduction of the fan beam; i.e., the second generation scanners and certainly it is not known that any have been used in third generation scanners even though there have been suggestions for using simultaneous dual slice acquisition with fourth generation machines. See, for example, an article entitled "Theoretical Possibilities for a CT Scanner Development" by Dr. D. P. Boyd, which was published in Diagnostic Imaging in December, 1982.

In general, the speed of scanning of computerized tomographic systems has increased from something like 5 minutes to less than a second. The increased speed has led to improved image quality; because among other things, of a reduction of motion caused artifacts. In addition the spatial resolution has improved due to increased computer power, and the number and density of the detectors. In the article, the problem of the additional cost of the detectors and hardware required for dual slice acquisition is addressed by the suggestion of the use of a plurality of X-ray sources displaced from each other in the Z direction rather than detectors displaced from each other in the Z direction. The Z direction is transverse to the longitudinal direction of the detector array or where the detector array is arcuate, the longitudinal direction of the top view planar projection of the detector array.

As witnessed by the fourth generation scanners, however, those skilled in the art are still searching for methods and apparatus to further decrease motion caused artifacts in addition to increasing the throughput and decreasing the exposure of the subject to radiation.

Accordingly, an object of the present invention is to provide a dual slice data acquisition system for use in third generation rotate-rotate computerized tomographic scanners.

BRIEF DESCRIPTION OF THE INVENTION

In accordance with the present invention a computerized tomographic system is provided, said system comprising:
  a gantry,
  said gantry including means for retaining X-ray source means on one side of a patient and X-ray detector means on the other side of said patient,
  means for simultaneously rotating said source means and said detector means about the patient,
  said detector means comprising means for simultaneously detecting X-rays that have traversed multiple plane sections in said patient,
  means for processing said detected X-rays to provide image data, and
  means for displaying images based on said image data.

A feature of the present invention provides means for more efficiently using the X-ray beams to obtain dual slice imaging data per scan. This efficient use of the X-ray beams speeds throughput, reduces motion caused artifacts and also reduces the patient's exposure to X-ray radiation without any undue adverse effects on the image quality. The dual slicing can be accomplished at a minimum increase in cost due to extra detectors by using two modes of operation, a single slice mode and a dual slice mode. The dual slice mode may be limited to scans less than whole body scans.

A related feature of the present invention provides means for shifting the detector means in the Z direction to assure that artifacts caused by beam divergence is readily correctable by using the familiar single slice scan geometry.

A further feature of the invention includes detector means wherein said means for simultaneously detecting X-rays that have traversed multiple plane sections in the patient comprises a pair of abutting detectors extending in the Z direction with means for isolating each of the detectors from affecting the juxtaposed detectors.

Where the Y direction is the direction between the source and the detectors and the X direction is the longitudinal direction of a detector array. The Z direction is perpendicular to both the X and the Y direction.

A further feature of the invention comprises utilizing a source means that has a dimension in the Z direction and thus is not a point source in the Z direction, said source means providing a fan beam which extends from the source means to the detector means and encompasses the patient in the X direction.

Another feature of the invention comprises utilizing multiple detectors extending in the Z direction only for a portion of the array in the X dimension. Thus, this utilization of limited extra detectors in the X direction extending in the Z direction minimizes the costs of extra detectors while providing the benefits of the dual slice capability in critical acquisition procedures, such as head scans.

BRIEF DESCRIPTION OF THE DRAWINGS

The above noted and other features and objects of the present invention will be best understood when considered in the light of the following description made in conjunction with the accompanying drawings, wherein.

GENERAL DESCRIPTION

Figure 1:
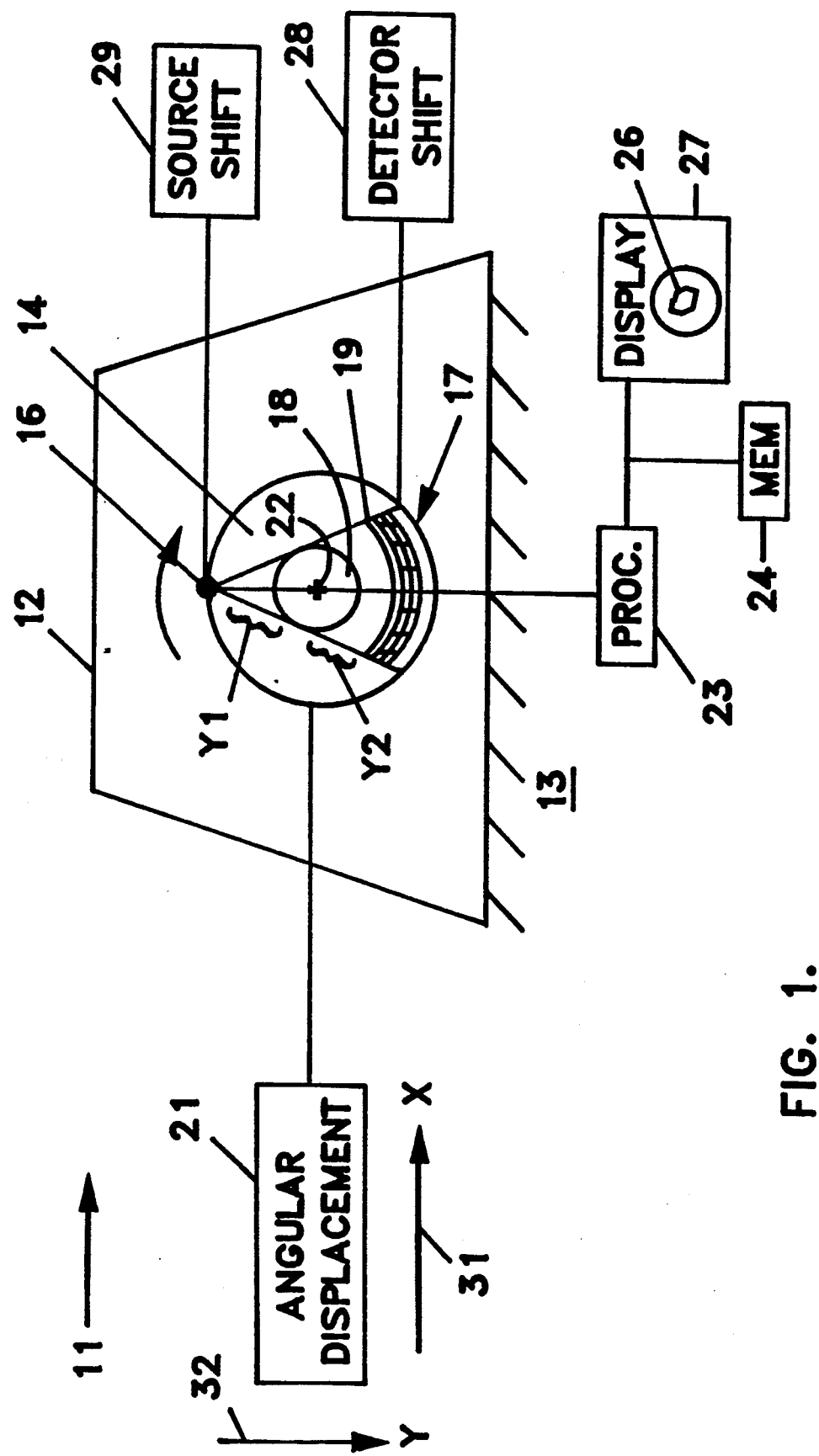
FIG. 1 is a partial block diagram which illustrates a CT scanner configuration according to the present invention.

In FIG. 1 a front end including the gantry of a rotate-rotate computerized tomographic scanner is shown at 11. The scanner comprises the gantry 12 mounted to a base 13. The gantry has an opening 14 for receiving the patient therein. An X-ray source means 16 is rotatably mounted on the gantry and is at a fixed distance from the detector array 17. Both the source means and the detector array 17 rotate together under the control of angular displacement means 21 about the patient 18, shown resting on a bed or cot 19.

The rotation is about the isocenter 22 shown at a distance Y1 from the source means and a distance Y2 from the detector array. Means such as processor 23 process the data from the detector array 17 utilizing memory means 24 to provide a display 26 on display means 27. Means for shifting the position of the detector relative to the source means, such as detector shift means 28 are shown for selectively shifting the detector in order to increase the effective spatial resolution of the system in a manner well known to those skilled in the art. It should be understood that the source means could be shifted instead of the detector means. The shift is relative to the source means 16.

To further increase the resolution in a preferred embodiment, the source means may be a dual focal spot source used in a manner described in U.S. Pat. No. 4,637,040 which issued on Jan. 13, 1987, and is assigned to the assignee of this invention. In addition the processing means includes means for minimizing non-coplanarity caused artifacts according to the system and methods taught by U.S. Pat. No. 4,578,753 which issued on Mar. 25, 1984, and is assigned to the assignee of this invention.

Non-coplanarity caused artifacts due to beam divergence are generally reduced to insignificance by scanning through 360 degrees. Alternatively, a source shifter 29 may be provided which shifts the source in the Z direction. It should be understood that the shifting of the source in the Z direction is relative to the detector array. Thus, the detector array can also be shifted in the Z direction. The shifting of the source in the Z direction is to locate the center of the source means at the junction point of the dual detectors in the detector array. Note that the source means is preferably centered over the center of the detector array in the X direction. The source means can be shifted so that its center in the Z direction is either over the center of the detector of the basic detector array or over the line of abutment of the dual detectors. The source means is over the center of detectors in the X direction without any shift. The means for shifting the source is indicated at block 29. Arrows indicating X and Y directions are shown at 31 and 32 respectively.

Figure 2:
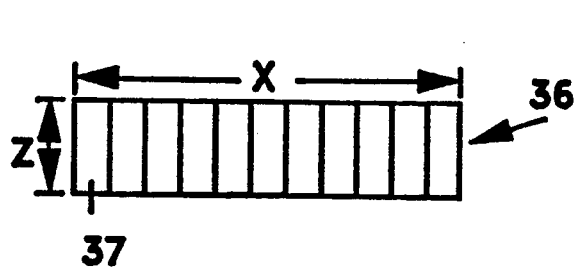
FIG. 2 is a simplified plan view of a prior art detector array.

FIG. 2 shows a prior art single row detector array at 36. The detector array is made up of a plurality of detectors, one of which is shown at 37. The array extends in the X direction while the length of the individual detectors extend in the Z direction. The prior art array is made up of single detectors in the Z direction.

Figure 3:
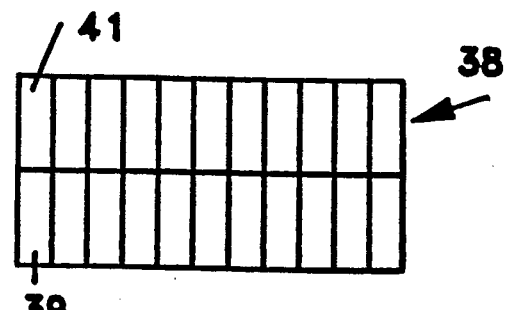
FIG. 3 is a simplified plan view of the detector array of the present invention.

A dual slice double row detector array is shown in FIG. 3 at 38. It is made up of a plurality of rows of detectors containing detectors such as detector 39 in a basic row abutting detector 41 in a second row. A plurality of such dual detectors are mounted in the array 38 to form the dual detector array. Care must be taken to avoid or minimize non-sensitive areas such as 42 of the abutting detectors that cannot acquire data because of light shielding. There must, however, be light shielding between detectors 39 and 41 to prevent scintillations in detector 39, for example, from affecting detector 41. The shielding can be accomplished in a collimator or by an actual shielding between the detectors 39 and 41. However, space between detectors such as space 42 between detectors 39 and 41 has to be kept to a minimum to avoid a loss of imaging areas and a consequent loss of image information between slices.

Figure 4:
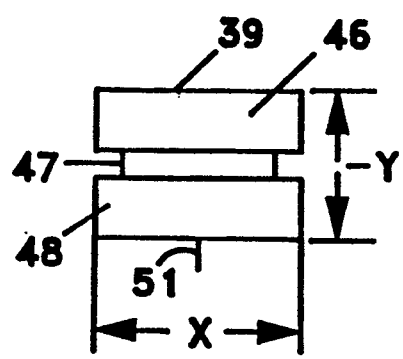
FIG. 4(a) shows details of the detector of FIG. 3 in a front view; i.e., along the X direction.
FIG. 4(b) shows details of the detectors of FIG. 3 in a side view; i.e., along the Z dimension.
Figure 4:
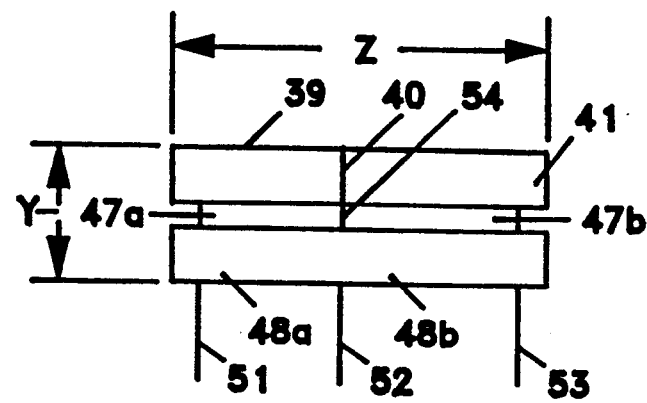

In FIGS. 4 the detectors 39 and 41 are shown. In FIG. 4a, there is a front view which particularly shows detector 39. FIG. 4b is the side view which shows both detectors 39 and 41. As shown in FIGS. 4a and 4b detectors 39 and 41 both comprise a crystal 46 which reacts to the impingement thereon of X-rays by expelling a quantum of light. The quantum of light strikes the photo-diode layer 47a, 47b respectively (FIG. 4b) which converts the light into electrical charges. It is important that quantums of light from the crystal 46a above one photo-diode 47a does not impinge the photo-diode 47b that is below crystal 46b. Therefore, shielding means 40 is provided between the crystals. The shielding means prevents quantum of light from crystals not directly above the photo-diodes from affecting these photo-diodes. The shielding may be such things as aluminum foil attached to the crystals at the abutment area or paint administered to the transparent crystals at the abutment area. The shield should be in the order of no more than 0.05 to 0.1 mm thick.

The electrical charges are received and transmitted by the electronic circuitry not shown but connected to support blocks 48(a) and 48(b). The support blocks 48a and 48b are connected to electronic circuitry over leads 51, 52 and 53 and from the electronic circuitry to the processor 23 which includes an analog to digital converter. Ideally leads 51 and 53 carry the electrons while lead 52 is connected to ground.

In a preferred embodiment the photo-diode substrate 47 is also divided into parts and optically separated at 54 to assure that there is no inter-action between the scintillations caused by X-rays striking either crystal 39 or 41. Thus, X-rays striking crystal 39 have almost no effect on photo-diode 47b. Similarly, X-rays striking crystal 41 have almost no effect on photo-diode 47a. The front end electronics provides analog signals which are converted into digital signals in the processor for processing into image data to provide the image 26 in display unit 27.

Figure 5:
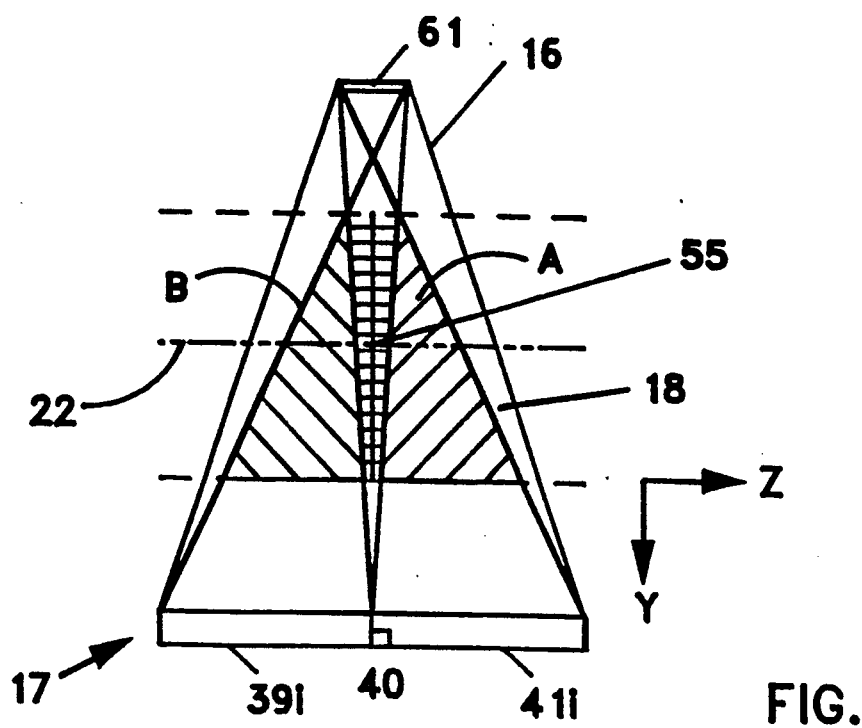
FIG. 5 shows a view in the YZ plane of the X-rays from the source means illuminating the detectors after passing through the patient.

As shown in the YZ plane of FIG. 5, ideally the source means shown at 16 has its center 61 aligned with the junction 40 of detectors 39i and 41i.

The distance between the source means at 16 and the detector array 17 extends in the Y direction. The isocenter 22 shown as a dot-dash line is indicated along with the patient 18. Notice that there is a crossover area 55 shown as cross-hatch section in the patient wherein data is obtained both by detector 39i and detector 41i. In the preferred embodiment, the dual focal spots mentioned earlier are located aligned with point 61 and extending in the X direction.

Figure 6:
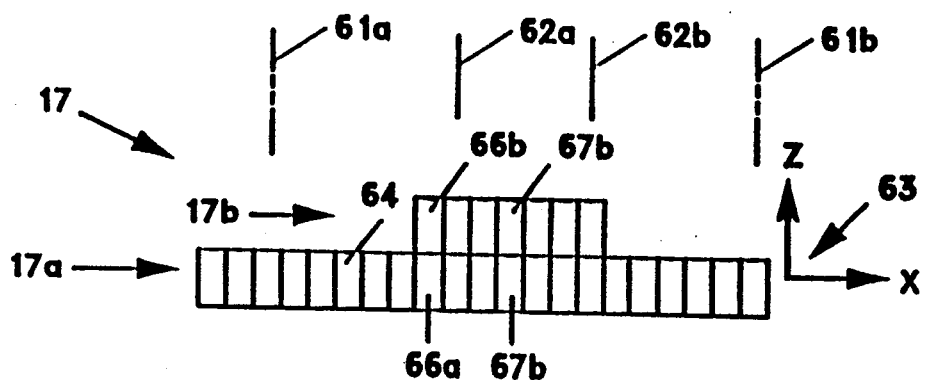
FIG. 6 is a plan view of another embodiment of the detector array in the inventive system.

A preferred embodiment of the detector array is shown in the plan view of FIG. 6. Therein the dual detectors are used only in a small portion of the array detector, sufficient for example, to cover the head of the patient. Thus, the array 17 is comprised of a basic or major detector array 17a which is the complete detector array and a minor detector array 17b comprising a reduced number of detectors which helps reduce the probability of partial volume artifacts.

The whole body fits between the dashed lines 61a and 61b. The head, for example, fits between the full lines 62a and 62b. The space between lines 62a and 62b is where partial volume artifacts can be significant.

The thickness of the dual slices is substantially the dimension of the detectors in the Z direction. The X and Z directions in FIG. 6 are shown at 63. The detector array of the type shown in FIG. 6 can also be used during the acquisition of multiple slices by moving either the patient or the source detector array assembly in a well known manner so as to obtain even contiguous slices.

Figure 7:
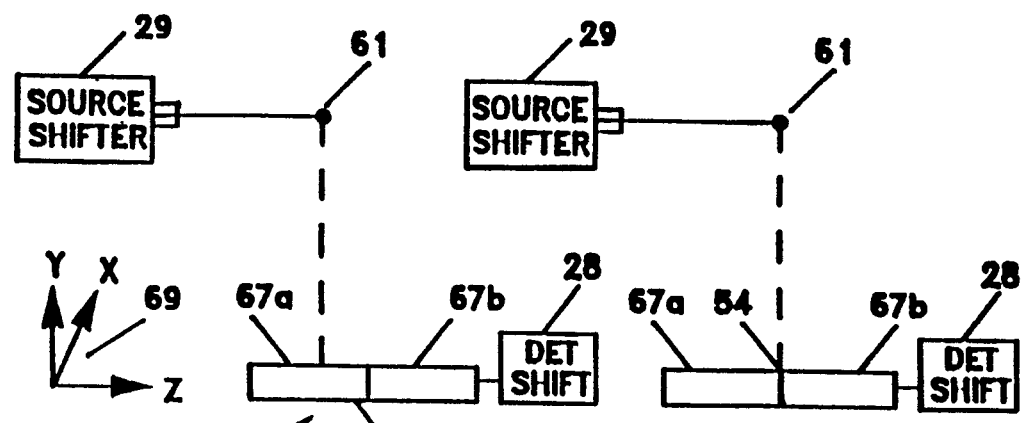
FIG. 7(a) shows a view in the YZ plane of the inventive detector array and source means with the source positioned to be over a first row of detectors.
FIG. 7(b) shows the source of FIG. 7(a) shifted to be over both a first and a second row of detectors.

FIG. 7 shows the shifting of the source relative to the detectors, or of the detectors relative to the source for example, detectors 67a and 67b. When the detector array 17a is used exclusively then the source is shifted or the detectors are shifted so that the center 61 of the source lies over the center 68 of detector 67a. When both detectors 67a and 67b are used then the source 16 is shifted or the detectors are shifted as shown in FIG. 7b so that the center 61 of the source is aligned with the junction area 40 of detectors 67a and 67b. The X, Y and Z axes are shown at 69.

Figure 8:
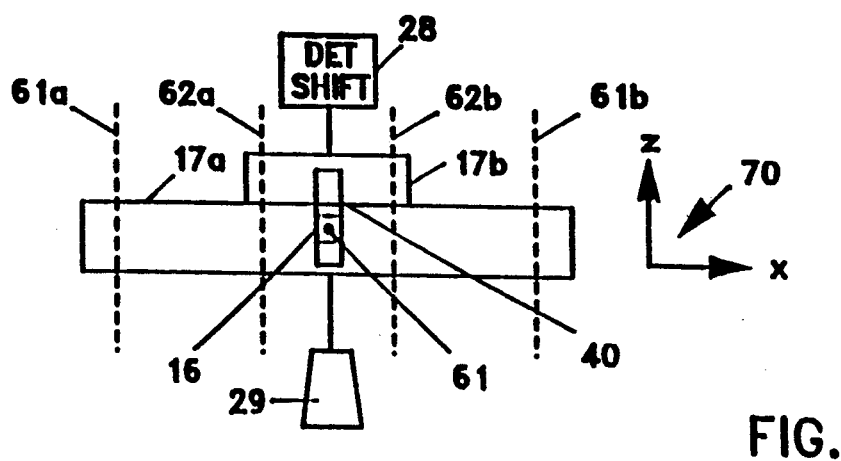
FIG. 8 is a plan view showing the source means in relation to the detector and the sections of the patient being imaged.

FIG. 8 is a plan view of the source detector arrangement showing the relationship between the source and the detectors in the different scanning modes. Thus, prior to scanning while utilizing detector array 17a then the source 16 is shifted so that its center point 61 is located in the middle of detector array 17a in the Z direction. The X and Z axes are shown at 70 in FIG. 8. The source shifter 29 shifts the source or the detector shifter 28 shifts the detector array so that the center point 61 is over the junction 40 between array 17a and 17b at the approximate center point in the X-direction of the detector array 17a.

In the preferred whole body scanning procedure the body appears between the lines 61a and 61b whereas the head or the spine, for example, appears between lines 62a and 62b in FIG. 8.

In practice, the patient rests on the cot and is moved into the scanner for obtaining a computerized tomographic scan. Dual slices are simultaneously obtained utilizing the rotate-rotate source detector arrangement. To minimize the number of detector needs utilization of a second detector array abutting the first detector array and having fewer detectors therein can be used. The second detector array is preferably, but not necessarily, aligned with the center of the source means in the X and Z directions.

The invention has been described in relation to specific procedures and embodiments, however, it should be understood that this description is made by way of example only and is not meant as a limitation on the scope of the invention.

What is claimed is:

1. A computerized tomographic (CT) scanner comprising:
    a patient holding means,
    a gantry,
    means for mounting an X-ray source on said gantry on one side of said patient holding means,
    means for mounting a partial ring of discrete X-ray detectors on the other side of said patient holding means,
        said partial ring of X-ray detectors comprising an array including two juxtaposed rows of discrete detectors for simultaneously detecting X-rays in a single scan that have traversed two juxtaposed planar sections in said patient,
        the partial ring of a first of said two rows being defined by the limits of a fan beam of X-ray radiation emanating from said source,
        means for simultaneously rotating said X-ray source and said detectors about the patient for more 180° per rotation in a rotate-rotate mode,
        means for generating images of said juxtaposed multiplanar sections in said patient with the detected X-rays from the single scan,
        means for shifting the partial ring of X-ray detectors relative to the X-ray source in the Z-direction where X, Y, and Z are directions in a Cartesian coordinate system with Y being the direction between the source and detectors, Z being the longitudinal direction of the patient holding means and X being the direction of rotation of the source and detectors, and said shifting means of the partial ring of X-ray detectors relative to the X-ray source occurring prior to the operation of the means for simultaneously rotating the X-ray source and said detectors for determining whether said two rows of detectors will be used or whether only one of said two rows of detectors will be used for detecting X-rays that have traversed said patient.

2. The CT scanner of claim 1 wherein said partial ring of a second row of said two rows being juxtaposed to the first row in the Z direction with both the first row and the second row of detectors extending in the X direction and being defined by the limits of the fan beam.

3. The CT scanner of claim 1 wherein the partial ring of the the second row is angularly smaller than the limits of the fan beam.

4. The CT scanner of claim 1 including shielding means for preventing interaction between said juxtaposed rows of detectors said shielding means being in the order of no more than 0.1 mm thick.

5. A method of selectively obtaining computerized tomographic (CT) image data from either a single slice in the patient or from two contiguous slices in the patient, said method comprising the steps of:
holding a patient,
mounting an X-ray source on one side of said patient,
mounting an X-ray detector means on the other side of said patient,
simultaneously rotating the X-ray source and said X-ray detector means about the patient more than 180° per rotation in a rotate-rotate mode, and
selectively detecting either X-rays that have simultaneously traversed two juxtaposed planar sections in said patient or X-rays that have traversed a single planar section in said patient.

6. The method of claim 5 including selectively shifting said detector means relative to said X-ray source in the Z direction; where X, Y and Z are directions in a Cartesian coordinate system with Y being the direction between the X-ray source and the detector means, Z being the longitudinal direction of the patient and with X being the direction of rotation and Z being normal to both the X and the Y directions.

7. The method of claim 6 including the step of shifting the detector means in the Z direction relative to the X-ray source so that only X-rays from the X-ray source that pass through only a single slice of the patient are detected.

8. The method of claim 6 including the step of shifting the detector means in the Z direction relative to the X-ray source so that X-rays from the X-ray source that pass through two contiguous slices are detected.

* * * * *